United States Patent
Dryga

(10) Patent No.: US 9,804,069 B2
(45) Date of Patent: Oct. 31, 2017

(54) METHODS FOR DEGRADING NUCLEIC ACID

(71) Applicant: DNAE Group Holdings Limited, London (GB)

(72) Inventor: Sergey A. Dryga, Albuquerque, NM (US)

(73) Assignee: DNAE Group Holdings Limited, London (GB)

(*) Notice: Subject to any disclaimer, the term of this patent is extended or adjusted under 35 U.S.C. 154(b) by 143 days.

(21) Appl. No.: 14/107,253

(22) Filed: Dec. 16, 2013

(65) Prior Publication Data

US 2014/0170021 A1  Jun. 19, 2014

Related U.S. Application Data

(60) Provisional application No. 61/739,593, filed on Dec. 19, 2012.

(51) Int. Cl.
*G01N 1/34* (2006.01)
*C12Q 1/68* (2006.01)

(52) U.S. Cl.
CPC ............ *G01N 1/34* (2013.01); *C12Q 1/6802* (2013.01)

(58) Field of Classification Search
CPC ...................................... C12Q 1/6802–1/6811
See application file for complete search history.

(56) References Cited

U.S. PATENT DOCUMENTS

| | | |
|---|---|---|
| 3,970,518 A | 7/1976 | Giaever |
| 4,018,886 A | 4/1977 | Giaever |
| 4,180,563 A | 12/1979 | Fauve |
| 4,230,685 A | 10/1980 | Senyei et al. |
| 4,267,234 A | 5/1981 | Rembaum |
| 4,434,237 A | 2/1984 | Dinarello |
| 4,452,773 A | 6/1984 | Molday |
| 4,551,435 A | 11/1985 | Liberti et al. |
| 4,554,088 A | 11/1985 | Whitehead et al. |
| 4,659,678 A | 4/1987 | Forrest et al. |
| 4,677,055 A | 6/1987 | Dodin et al. |
| 4,683,195 A | 7/1987 | Mullis et al. |
| 4,683,202 A | 7/1987 | Mullis |
| 4,695,393 A | 9/1987 | Chagnon et al. |
| 4,795,698 A | 1/1989 | Owen et al. |
| 4,901,018 A | 2/1990 | Lew |
| 4,925,788 A | 5/1990 | Liberti |
| 4,942,124 A | 7/1990 | Church |
| 4,988,617 A | 1/1991 | Landegren et al. |
| 5,047,321 A | 9/1991 | Loken et al. |
| 5,057,413 A | 10/1991 | Terstappen et al. |
| 5,089,386 A | 2/1992 | Stackebrandt et al. |
| 5,108,933 A | 4/1992 | Liberti et al. |
| 5,118,603 A * | 6/1992 | Popp ............... A61L 2/0088 435/6.11 |
| 5,136,095 A | 8/1992 | Tarnowski et al. |
| 5,149,625 A | 9/1992 | Church et al. |
| 5,164,297 A | 11/1992 | Josephson et al. |
| 5,186,827 A | 2/1993 | Liberti et al. |
| 5,200,084 A | 4/1993 | Liberti et al. |
| 5,229,724 A | 7/1993 | Zeiger |
| 5,234,816 A | 8/1993 | Terstappen |
| 5,242,794 A | 9/1993 | Whiteley et al. |
| 5,254,460 A | 10/1993 | Josephson et al. |
| 5,338,687 A | 8/1994 | Lee et al. |
| 5,342,790 A | 8/1994 | Levine et al. |
| 5,460,979 A | 10/1995 | Levine et al. |
| 5,466,574 A | 11/1995 | Liberti et al. |
| 5,494,810 A | 2/1996 | Barany et al. |
| 5,512,332 A | 4/1996 | Liberti et al. |
| 5,541,072 A | 7/1996 | Wang et al. |
| 5,583,024 A | 12/1996 | McElroy et al. |
| 5,583,033 A | 12/1996 | Terstappen et al. |
| 5,597,531 A | 1/1997 | Liberti et al. |
| 5,604,097 A | 2/1997 | Brenner |
| 5,605,805 A | 2/1997 | Verwer et al. |
| 5,622,831 A | 4/1997 | Liberti et al. |
| 5,622,853 A | 4/1997 | Terstappen et al. |
| 5,636,400 A | 6/1997 | Young |

(Continued)

FOREIGN PATENT DOCUMENTS

| | | |
|---|---|---|
| CA | 2 342 047 A1 | 9/2001 |
| EP | 1 304 581 A2 | 4/2003 |

(Continued)

OTHER PUBLICATIONS

Mulder, et al., Characterization of two human monoclonal antibodies reactive with HLA-B12 and HLA-B60, respectively, raised by in vitro secondary immunization of peripheral blood lymphocytes, Hum. Immunol., 36(3):186-192 (1993).
Nyquist, Thermal Agitation of Electrical Charge in Conductors, Phys. Rev., 32:110-113 (1928).
Margin, et al., High resolution microcoil 1H-NMR for mass-limited, nanoliter-volume samples, Science, 270:1967 (1995).
Olson, et al., High-resolution microcoil NMR for analysis of mass-limited, nanoliter samples, Anal. Chem., 70:645-650 (1998).
Pappas, et al., Cellular Separations: A Review of New Challenges in Analytical Chemistry, Analytica Chimica Acta, 601(1):26-35 (2007).
Peck, et al., Design and Analysis of Microcoils for NMR Microscopy, J. Magn. Reson. B 108:114-124 (1995).

(Continued)

*Primary Examiner* — Sean E Conley
*Assistant Examiner* — Matthew Krcha
(74) *Attorney, Agent, or Firm* — Brown Rudnick LLP; Thomas C. Meyers

(57) ABSTRACT

Methods for degrading contaminant nucleic acid. The methods use combinations of metal ions and peroxide ions to produce a variety of oxidative species that degrade nucleic acid. Methods of the invention are useful for decontaminating laboratory equipment or solutions. After the equipment or solutions have been decontaminated, the metal ion and peroxide ion solution can be deactivated by raising the temperature to dissociate the peroxide or by binding the metal ions, e.g., with a chelating agent.

26 Claims, No Drawings

(56) References Cited

U.S. PATENT DOCUMENTS

| | | |
|---|---|---|
| 5,646,001 A | 7/1997 | Terstappen et al. |
| 5,654,636 A | 8/1997 | Sweedler et al. |
| 5,660,990 A | 8/1997 | Rao et al. |
| 5,674,713 A | 10/1997 | McElroy et al. |
| 5,677,133 A | 10/1997 | Oberhardt |
| 5,681,478 A | 10/1997 | Lea et al. |
| 5,684,401 A | 11/1997 | Peck et al. |
| 5,695,934 A | 12/1997 | Brenner |
| 5,695,946 A | 12/1997 | Benjamin et al. |
| 5,698,271 A | 12/1997 | Liberti et al. |
| 5,700,673 A | 12/1997 | McElroy et al. |
| 5,741,714 A | 4/1998 | Liberti |
| 5,768,089 A | 6/1998 | Finnigan |
| 5,770,461 A | 6/1998 | Sakazume et al. |
| 5,773,307 A | 6/1998 | Colin et al. |
| 5,776,710 A | 7/1998 | Levine et al. |
| 5,795,470 A | 8/1998 | Wang et al. |
| 5,821,066 A | 10/1998 | Pyle et al. |
| 5,834,217 A | 11/1998 | Levine et al. |
| 5,840,580 A | 11/1998 | Terstappen et al. |
| 5,846,719 A | 12/1998 | Brenner et al. |
| 5,858,650 A * | 1/1999 | Celebuski ............ C07D 471/08 435/6.1 |
| 5,863,722 A | 1/1999 | Brenner |
| 5,866,099 A | 2/1999 | Owen et al. |
| 5,869,252 A | 2/1999 | Bouma et al. |
| 5,876,593 A | 3/1999 | Liberti et al. |
| 5,925,573 A | 7/1999 | Colin et al. |
| 5,935,825 A | 8/1999 | Nishimura et al. |
| 5,948,412 A | 9/1999 | Murphy |
| 5,955,583 A | 9/1999 | Beavo et al. |
| 5,961,879 A * | 10/1999 | Trigiante ............ C01B 11/068 252/187.25 |
| 5,985,153 A | 11/1999 | Dolan et al. |
| 5,993,665 A | 11/1999 | Terstappen et al. |
| 6,013,188 A | 1/2000 | Terstappen et al. |
| 6,013,532 A | 1/2000 | Liberti et al. |
| 6,060,882 A | 5/2000 | Doty |
| 6,097,188 A | 8/2000 | Sweedler et al. |
| 6,100,099 A | 8/2000 | Gordon et al. |
| 6,120,856 A | 9/2000 | Liberti et al. |
| 6,136,182 A | 10/2000 | Dolan et al. |
| 6,138,077 A | 10/2000 | Brenner |
| 6,146,838 A | 11/2000 | Williams et al. |
| 6,150,516 A | 11/2000 | Brenner et al. |
| 6,172,214 B1 | 1/2001 | Brenner |
| 6,172,218 B1 | 1/2001 | Brenner |
| 6,194,900 B1 | 2/2001 | Freeman et al. |
| 6,228,624 B1 | 5/2001 | Terstappen |
| 6,235,475 B1 | 5/2001 | Brenner et al. |
| 6,236,205 B1 | 5/2001 | Ludeke et al. |
| 6,242,915 B1 | 6/2001 | Hurd |
| 6,265,150 B1 | 7/2001 | Terstappen et al. |
| 6,287,791 B1 | 9/2001 | Terstappen et al. |
| 6,307,372 B1 | 10/2001 | Sugarman et al. |
| 6,326,787 B1 | 12/2001 | Cowgill |
| 6,348,318 B1 | 2/2002 | Valkirs |
| 6,352,828 B1 | 3/2002 | Brenner |
| 6,361,749 B1 | 3/2002 | Terstappen et al. |
| 6,361,944 B1 | 3/2002 | Mirkin et al. |
| 6,365,362 B1 | 4/2002 | Terstappen et al. |
| 6,397,094 B1 | 5/2002 | Ludeke et al. |
| 6,404,193 B1 | 6/2002 | Dourdeville |
| 6,456,072 B1 | 9/2002 | Webb et al. |
| 6,469,636 B1 | 10/2002 | Baird et al. |
| 6,487,437 B1 | 11/2002 | Viswanathan et al. |
| 6,495,357 B1 | 12/2002 | Fuglsang et al. |
| 6,512,941 B1 | 1/2003 | Weiss et al. |
| 6,514,415 B2 | 2/2003 | Hatch et al. |
| 6,551,843 B1 | 4/2003 | Rao et al. |
| 6,555,324 B1 | 4/2003 | Olweus et al. |
| 6,582,938 B1 | 6/2003 | Su et al. |
| 6,587,706 B1 | 7/2003 | Viswanathan |
| 6,594,517 B1 | 7/2003 | Nevo |
| 6,620,627 B1 | 9/2003 | Liberti et al. |
| 6,623,982 B1 | 9/2003 | Liberti et al. |
| 6,623,983 B1 | 9/2003 | Terstappen et al. |
| 6,645,731 B2 | 11/2003 | Terstappen et al. |
| 6,660,159 B1 | 12/2003 | Terstappen et al. |
| 6,696,838 B2 | 2/2004 | Raftery et al. |
| 6,700,379 B2 | 3/2004 | Peck et al. |
| 6,788,061 B2 | 9/2004 | Sweedler et al. |
| 6,790,366 B2 | 9/2004 | Terstappen et al. |
| 6,818,395 B1 | 11/2004 | Quake et al. |
| 6,822,454 B2 | 11/2004 | Peck et al. |
| 6,845,262 B2 | 1/2005 | Albert et al. |
| 6,858,384 B2 | 2/2005 | Terstappen et al. |
| 6,867,021 B2 | 3/2005 | Maes et al. |
| 6,876,200 B2 | 4/2005 | Anderson et al. |
| 6,890,426 B2 | 5/2005 | Terstappen et al. |
| 6,898,430 B1 | 5/2005 | Liberti et al. |
| 6,914,538 B2 | 7/2005 | Baird et al. |
| 6,958,609 B2 | 10/2005 | Raftery et al. |
| 7,011,794 B2 | 3/2006 | Kagan et al. |
| 7,056,657 B2 | 6/2006 | Terstappen et al. |
| 7,078,224 B1 | 7/2006 | Bitner et al. |
| 7,096,057 B2 | 8/2006 | Hockett et al. |
| 7,141,978 B2 | 11/2006 | Peck et al. |
| 7,169,560 B2 | 1/2007 | Lapidus et al. |
| 7,200,430 B2 | 4/2007 | Thomas et al. |
| 7,202,667 B2 | 4/2007 | Barbic |
| RE39,793 E | 8/2007 | Brenner |
| 7,271,592 B1 | 9/2007 | Gerald, II et al. |
| 7,274,191 B2 | 9/2007 | Park et al. |
| 7,282,180 B2 | 10/2007 | Tibbe et al. |
| 7,282,337 B1 | 10/2007 | Harris |
| 7,282,350 B2 | 10/2007 | Rao et al. |
| 7,304,478 B2 | 12/2007 | Tsuda et al. |
| 7,332,288 B2 | 2/2008 | Terstappen et al. |
| 7,345,479 B2 | 3/2008 | Park et al. |
| 7,393,665 B2 | 7/2008 | Brenner |
| 7,403,008 B2 | 7/2008 | Blank et al. |
| 7,405,567 B2 | 7/2008 | McDowell |
| 7,523,385 B2 | 4/2009 | Nguyen et al. |
| 7,537,897 B2 | 5/2009 | Brenner et al. |
| 7,544,473 B2 | 6/2009 | Brenner |
| 7,564,245 B2 | 7/2009 | Lee |
| 7,666,308 B2 | 2/2010 | Scholtens et al. |
| 7,688,777 B2 | 3/2010 | Liberti, Jr. et al. |
| 7,764,821 B2 | 7/2010 | Coumans et al. |
| 7,815,863 B2 | 10/2010 | Kagan et al. |
| 7,828,968 B2 | 11/2010 | Tibbe et al. |
| 7,863,012 B2 | 1/2011 | Rao et al. |
| 7,901,950 B2 | 3/2011 | Connelly et al. |
| 7,943,397 B2 | 5/2011 | Tibbe et al. |
| 8,067,938 B2 | 11/2011 | McDowell |
| 8,102,176 B2 | 1/2012 | Lee |
| 8,110,101 B2 | 2/2012 | Tibbe et al. |
| 8,111,669 B2 | 2/2012 | Liberti, Jr. et al. |
| 8,128,890 B2 | 3/2012 | Droog et al. |
| 8,841,104 B2 | 9/2014 | Dryga et al. |
| 8,889,368 B2 | 11/2014 | Barbreau et al. |
| 2001/0018192 A1 | 8/2001 | Terstappen et al. |
| 2002/0009759 A1 | 1/2002 | Terstappen et al. |
| 2002/0012669 A1 | 1/2002 | Presnell et al. |
| 2002/0098531 A1 | 7/2002 | Thacker |
| 2002/0130661 A1 | 9/2002 | Raftery et al. |
| 2002/0132228 A1 | 9/2002 | Terstappen et al. |
| 2002/0141913 A1 | 10/2002 | Terstappen et al. |
| 2002/0164629 A1 | 11/2002 | Quake et al. |
| 2002/0164659 A1 | 11/2002 | Rao et al. |
| 2002/0172987 A1 | 11/2002 | Terstappen et al. |
| 2003/0003441 A1 | 1/2003 | Colston et al. |
| 2003/0022231 A1 | 1/2003 | Wangh et al. |
| 2003/0054376 A1 | 3/2003 | Mullis et al. |
| 2003/0088181 A1 | 5/2003 | Gleich |
| 2003/0092029 A1 | 5/2003 | Josephson et al. |
| 2003/0129676 A1 | 7/2003 | Terstappen et al. |
| 2003/0138838 A1 * | 7/2003 | Wang .................. C12Q 1/6837 435/6.12 |
| 2003/0203507 A1 | 10/2003 | Liberti et al. |
| 2003/0206577 A1 | 11/2003 | Liberti et al. |
| 2003/0215818 A1 * | 11/2003 | Lorenz .................. C07H 21/04 435/6.11 |

(56) References Cited

U.S. PATENT DOCUMENTS

| | | |
|---|---|---|
| 2003/0222648 A1 | 12/2003 | Fan |
| 2004/0004043 A1 | 1/2004 | Terstappen et al. |
| 2004/0018611 A1 | 1/2004 | Ward et al. |
| 2004/0033916 A1* | 2/2004 | Kuzmin .......... A01N 59/16 510/161 |
| 2004/0072269 A1 | 4/2004 | Rao et al. |
| 2004/0076990 A1 | 4/2004 | Picard et al. |
| 2004/0087032 A1 | 5/2004 | Chandler et al. |
| 2004/0101443 A1 | 5/2004 | Kagan et al. |
| 2004/0118757 A1 | 6/2004 | Terstappen et al. |
| 2004/0151629 A1 | 8/2004 | Pease et al. |
| 2005/0003464 A1 | 1/2005 | Tibbe et al. |
| 2005/0006990 A1 | 1/2005 | Williquette et al. |
| 2005/0026144 A1 | 2/2005 | Maes et al. |
| 2005/0037351 A1* | 2/2005 | Kanno .......... C12N 15/1017 435/6.11 |
| 2005/0043521 A1 | 2/2005 | Terstappen et al. |
| 2005/0069900 A1 | 3/2005 | Lentrichia |
| 2005/0079520 A1 | 4/2005 | Wu |
| 2005/0111414 A1 | 5/2005 | Liberti et al. |
| 2005/0128985 A1 | 6/2005 | Liberti et al. |
| 2005/0181353 A1 | 8/2005 | Rao et al. |
| 2005/0181463 A1 | 8/2005 | Rao et al. |
| 2005/0202491 A1* | 9/2005 | Nelson .......... A61L 2/186 435/6.17 |
| 2005/0245814 A1 | 11/2005 | Anderson et al. |
| 2006/0024756 A1 | 2/2006 | Tibbe et al. |
| 2006/0105930 A1* | 5/2006 | McDonnell .......... A01N 59/00 510/161 |
| 2006/0115380 A1 | 6/2006 | Kagan et al. |
| 2006/0129327 A1 | 6/2006 | Kim et al. |
| 2006/0147901 A1 | 7/2006 | Jan et al. |
| 2006/0194192 A1 | 8/2006 | Rao et al. |
| 2006/0233712 A1 | 10/2006 | Penades et al. |
| 2006/0257847 A1 | 11/2006 | Scholtens et al. |
| 2006/0257945 A1 | 11/2006 | Masters et al. |
| 2006/0281094 A1 | 12/2006 | Squirrell et al. |
| 2007/0037173 A1 | 2/2007 | Allard et al. |
| 2007/0037231 A1 | 2/2007 | Sauer-Budge et al. |
| 2007/0090836 A1 | 4/2007 | Xiang et al. |
| 2007/0114181 A1 | 5/2007 | Li et al. |
| 2007/0116602 A1 | 5/2007 | Lee |
| 2007/0117158 A1 | 5/2007 | Coumans et al. |
| 2007/0152669 A1 | 7/2007 | Park et al. |
| 2007/0152670 A1 | 7/2007 | Park et al. |
| 2007/0154960 A1 | 7/2007 | Connelly et al. |
| 2007/0166835 A1 | 7/2007 | Bobrow et al. |
| 2007/0183935 A1 | 8/2007 | Clemmens et al. |
| 2007/0231926 A1 | 10/2007 | Ikeda |
| 2007/0296413 A1 | 12/2007 | Park et al. |
| 2008/0026451 A1 | 1/2008 | Braman et al. |
| 2008/0042650 A1 | 2/2008 | McDowell |
| 2008/0081330 A1 | 4/2008 | Kahvejian |
| 2008/0099715 A1 | 5/2008 | Adams et al. |
| 2008/0113350 A1 | 5/2008 | Terstappen |
| 2008/0199851 A1 | 8/2008 | Egan et al. |
| 2008/0204011 A1 | 8/2008 | Shoji |
| 2008/0204022 A1 | 8/2008 | Sillerud et al. |
| 2008/0272788 A1 | 11/2008 | McDowell |
| 2008/0286838 A1 | 11/2008 | Yuan et al. |
| 2008/0315875 A1 | 12/2008 | Sillerud |
| 2009/0026082 A1 | 1/2009 | Rothberg et al. |
| 2009/0061456 A1 | 3/2009 | Allard et al. |
| 2009/0061476 A1 | 3/2009 | Tibbe et al. |
| 2009/0061477 A1 | 3/2009 | Tibbe et al. |
| 2009/0127589 A1 | 5/2009 | Rothberg et al. |
| 2009/0134869 A1 | 5/2009 | Lee |
| 2009/0136946 A1 | 5/2009 | Connelly et al. |
| 2009/0146658 A1 | 6/2009 | McDowell et al. |
| 2009/0148847 A1 | 6/2009 | Kokoris et al. |
| 2009/0156572 A1 | 6/2009 | Ikeura et al. |
| 2009/0173681 A1 | 7/2009 | Siddiqi |
| 2009/0191535 A1 | 7/2009 | Connelly et al. |
| 2009/0227044 A1 | 9/2009 | Dosev et al. |
| 2009/0246796 A1 | 10/2009 | Bernard et al. |
| 2009/0256572 A1 | 10/2009 | McDowell |
| 2009/0258365 A1 | 10/2009 | Terstappen et al. |
| 2009/0286264 A1 | 11/2009 | Scholtens et al. |
| 2010/0035252 A1 | 2/2010 | Rothberg et al. |
| 2010/0068723 A1 | 3/2010 | Jovanovich et al. |
| 2010/0072994 A1 | 3/2010 | Lee et al. |
| 2010/0086976 A1* | 4/2010 | Paranhos-Baccala C12Q 1/6848 435/91.2 |
| 2010/0129785 A1 | 5/2010 | Pris et al. |
| 2010/0137143 A1 | 6/2010 | Rothberg et al. |
| 2010/0144005 A1 | 6/2010 | Bin Kingombe et al. |
| 2010/0188073 A1 | 7/2010 | Rothberg et al. |
| 2010/0197507 A1 | 8/2010 | Rothberg et al. |
| 2010/0219824 A1 | 9/2010 | Sillerud et al. |
| 2010/0225315 A1 | 9/2010 | McDowell |
| 2010/0282617 A1 | 11/2010 | Rothberg et al. |
| 2010/0282788 A1 | 11/2010 | Liberti |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2010/0304982 A1 | 12/2010 | Hinz et al. |
| 2010/0326587 A1 | 12/2010 | Kagan et al. |
| 2011/0014686 A1 | 1/2011 | Tibbe et al. |
| 2011/0018538 A1 | 1/2011 | Lee |
| 2011/0044527 A1 | 2/2011 | Tibbe et al. |
| 2011/0046475 A1 | 2/2011 | Assif et al. |
| 2011/0052037 A1 | 3/2011 | Coumans et al. |
| 2011/0059444 A1 | 3/2011 | Stromberg et al. |
| 2011/0070586 A1 | 3/2011 | Slezak et al. |
| 2011/0086338 A1 | 4/2011 | Hwang et al. |
| 2011/0091987 A1 | 4/2011 | Weissleder et al. |
| 2011/0098623 A1 | 4/2011 | Zhang et al. |
| 2011/0104718 A1 | 5/2011 | Rao et al. |
| 2011/0183398 A1 | 7/2011 | Dasaratha et al. |
| 2011/0262893 A1 | 10/2011 | Dryga et al. |
| 2011/0262925 A1 | 10/2011 | Dryga et al. |
| 2011/0262926 A1 | 10/2011 | Esch et al. |
| 2011/0262927 A1 | 10/2011 | Dryga et al. |
| 2011/0262932 A1 | 10/2011 | Esch et al. |
| 2011/0262933 A1 | 10/2011 | Dryga et al. |
| 2011/0262989 A1 | 10/2011 | Clarizia et al. |
| 2011/0263833 A1 | 10/2011 | Dryga et al. |
| 2011/0300551 A1 | 12/2011 | Rao et al. |
| 2011/0301042 A1 | 12/2011 | Steinmann et al. |
| 2012/0045828 A1 | 2/2012 | Davis et al. |
| 2012/0094275 A1 | 4/2012 | Rao et al. |
| 2012/0095178 A1* | 4/2012 | Pressel .......... A61L 2/186 526/255 |
| 2012/0100546 A1 | 4/2012 | Lowery, Jr. et al. |
| 2012/0112744 A1 | 5/2012 | McDowell et al. |
| 2012/0301926 A1* | 11/2012 | Chen .......... C12Q 1/6806 435/91.5 |
| 2013/0109590 A1 | 5/2013 | Clarizia et al. |
| 2013/0196341 A1 | 8/2013 | Neely et al. |
| 2013/0203634 A1 | 8/2013 | Jovanovich et al. |
| 2013/0316355 A1 | 11/2013 | Dryga et al. |
| 2014/0100136 A1 | 4/2014 | Clarizia et al. |
| 2014/0170021 A1 | 6/2014 | Dryga |
| 2014/0170639 A1 | 6/2014 | Norvell |
| 2014/0170640 A1 | 6/2014 | Dykes |
| 2014/0170641 A1 | 6/2014 | Macemon |
| 2014/0170652 A1 | 6/2014 | Sitdikov et al. |
| 2014/0170667 A1 | 6/2014 | Dykes et al. |
| 2014/0170669 A1 | 6/2014 | Vandervest |
| 2014/0170727 A1 | 6/2014 | Dryga et al. |
| 2014/0171340 A1 | 6/2014 | Dykes et al. |
| 2015/0212079 A1 | 7/2015 | Dryga et al. |

FOREIGN PATENT DOCUMENTS

| | | |
|---|---|---|
| WO | 89/06699 A1 | 7/1989 |
| WO | 90/08841 A1 | 8/1990 |
| WO | 91/02811 A1 | 3/1991 |
| WO | 92/08805 A1 | 5/1992 |
| WO | 92/15883 A1 | 9/1992 |
| WO | 95/31481 A1 | 11/1995 |
| WO | 98/20148 A1 | 5/1998 |
| WO | 99/53320 A1 | 10/1999 |
| WO | 01/73460 A1 | 10/2001 |

(56) References Cited

FOREIGN PATENT DOCUMENTS

| WO | 02/098364 | A2 | 12/2002 |
|---|---|---|---|
| WO | 2005/026762 | A1 | 3/2005 |
| WO | 2005106480 | A1 | 11/2005 |
| WO | 2007/018601 | A1 | 2/2007 |
| WO | 2007/123345 | A1 | 11/2007 |
| WO | 2007/135099 | A1 | 11/2007 |
| WO | 2007123342 | A1 | 11/2007 |
| WO | 2008/119054 | A1 | 10/2008 |
| WO | 2008/139419 | A1 | 11/2008 |
| WO | 2009/048673 | A2 | 4/2009 |
| WO | 2009/055587 | A1 | 4/2009 |
| WO | 2009/122216 | A1 | 10/2009 |
| WO | 2011/019874 | A1 | 2/2011 |
| WO | 2011/133630 | A1 | 10/2011 |
| WO | 2011/133632 | A1 | 10/2011 |
| WO | 2011/133759 | A1 | 10/2011 |
| WO | 2011/133760 | A1 | 10/2011 |

OTHER PUBLICATIONS

Peck, et al., RF Microcoils patterned using microlithographic techniques for use as microsensors in NMR, Proc. 15th Ann. Int. Conf. of the IEEE, Oct. 28-31, pp. 174-175 (1993).
Perez, et al., Viral-induced self-assembly of magnetic nanoparticle allows detection of viral particles in biological media, J. Am. Chem. Soc., 125:10192-10193 (2003).
Qiu, et al., Immunomagnetic separation and rapid detection of bacteria using bioluminescence and microfluidics, Talanta, 79:787-795 (2009).
Rogers, et al., Using microcontact printing to fabricate microcoils on capillaries for high resolution proton nuclear magnetic resonance on nanoliter volumes, Appl. Phys. Lett., 70:2464-2466 (1997).
Seeber, et al., Design and Testing of high sensitivity Microreceiver Coil Apparatus for Nuclear Magnetic Resonance and Imaging, Rev. Sci. Inst., 72:2171-2179 (2001).
Seeber, et al., Triaxial Magnetic Field Gradient System for Microcoil Magnetic Resonance Imaging, Rev. Sci. Inst., 71:4263-4272 (2000).
Sillerud, et al., 1H NMR Detection of Superparamagnetic Nanoparticles at 1 T using a Microcoil and Novel Tuning Circuit, J. Magn. Reson. 181:181-190 (2006).
Skjerve, et al., Detection of Listeria monocytogenes in foods by immunomagnetic separation, Appl. Env. Microbiol., 56:3478 (1990).
Sorli, et al., Micro-spectrometer for NMR: analysis of small quantities in vitro, Meas. Sci. Technol., 15:877-880 (2004).
Stanley, Essentials in Immunology and Serology, Delmar, pp. 153-153 (2002).
Stauber, et al. Rapid generation of monoclonal antibody-secreting hybridomas against African horse sickness virus by in vitro immunization and the fusion/cloning technique, J. Immunol. Methods, 161(2):157-168 (1993).
Stocker, et al. Nanoliter volume, high-resolution NMR Microspectroscopy using a 60 um planer microcoil, IEEE Trans. Biomed. Eng., 44:1122-1127 (1997).
Subramanian, et al., RF Microcoil Design for Practical NMR of Mass-Limited Samples, J. Magn. Reson., 133:227-231 (1998).
Taktak, et al., Multiparameter Magnetic Relaxation Switch Assays, Analytical Chemistry, 79(23):8863-8869 (2007).
Torensama, et al., Monoclonal Antibodies Specific for the Phase-Variant O-Acetylated Ki Capsule of Escerichia coli, J. Clin. Microbiol., 29(7):1356-1358 (1991).
Trumbull, et al., Integrating microfabricated fluidic systems and NMR spectroscopy, IEEE Trans. Biomed. Eng., 47(1):3-7 (2000).
Van Bentum, et al., Towards Nuclear Magnetic Resonance (MU)-Spectroscopy and (MU)-Imaging, Analyst, Royal Society of Chemistry, London, 129(9):793-803 (2004).
Venkateswaran, et al., Production of Anti-Fibroblast Growth Factor Receptor Monoclonal Antibodies by In Vitro Immunization, Hybridoma, 11(6):729-739 (1992).
Vermunt, et al., Isolation of salmonelas by immunomagnetic separation, J. Appl. Bact., 72:112-118 (1992).
Wang and Irudayaraj, Multifunctional Magnetic-Optical Nanoparticle Probes for Simultaneous Detection, Separation, and Thermal Ablation of Multiple Pathogens, Small, 6(2):283-289 (2010).
Webb and Grant, Signal-to-Noise and Magnetic Susceptibility Trade-offs in Solenoidal Microcoils for NMR, J. Magn. Reson. B, 113:83-87 (1996).
Wensink, et al., High Signal to Noise Ratio in Low-field NMR on a Chip: Simulations and Experimental Results, 17th IEEE MEMS, 407-410 (2004).
Williams and Wang, Microfabrication of an electromagnetic power micro-relay using SU-8 based UV-LIGA technology, Microsystem Technologies, 10(10):699-705 (2004).
Wu, et al., 1H-NMR Spectroscopy on the Nanoliter Scale for Static and On-Line Measurements, Anal. Chem., 66:3849 (1994).
Zhao, et al. A rapid bioassay for single bacterial cell quantitation using bioconjugated nanoparticles, PNAS, 101(42):15027-15032 (2004).
Zordan, et al., Detection of Pathogenic E. coli O157:H7 by a Hybrid Microfluidic SPR and Molecular Imaging Cytometry Device, Cytometry A, 75A:155-162 (2009).
Extended European Search Report, dated Oct. 15, 2013 for EP application No. 11772606.7.
International Search Report issued in PCT/US2013/076649, dated Feb. 27, 2014.
Chungang Wang et al. "Multifunctional Magnetic-OPtical Nanoparticle Probes for Simultaneous Detection, Separation, and Thermal Ablation of Multiple Pathogens", Small, vol. 6, No. 2 Jan. 18, 2010, pp. 283-289.
Madonna A J, et al. "Detection of Bacteria from Biological Mixtures Using Immunomagnetic Separation Combined with Matrix-Assisted Laser Desorption/Ionization Time-of-flight Mass Spectrometry", Rapid Communications in Mass Spectrometry, John Wiley & Sons, GB, vol. 15, No. 13, Jan. 1, 2001, pp. 1068-1074.
Extended European Search Report issued in EP 11864030.9, dated Aug. 20, 2014.
Fung, M-C., et al. PCR amplification of mRNA directly from a crude cell lysate prepared by thermophilic protease digestion, Nucleic Acids Research, vol. 19 (15), p. 4300, 1991.
Dynabeads® for Immunoassay IVD, retrieved from http://www.invitrogen.com/site/i3s/en/home/Products-and-Services/Applications/DiagnosticsClinical-Research/Bead-based-IVD-Assays/Bead-based-Immunoassav-iVD.html on May 29, 2013, four pages).
Burtis et al. (Burtis, C.A. (Ed.), Tietz Textbook of Clinical Chemistry, 3rd Edition (1999), W.B. Saunders Company, Philadelphia, PA, pp. 1793-1794).
Cooper et al., 2011, A micromagnetic flux concentrator device for isolation and visualization of pathogens. 15th International Conference on Miniaturized Systems for Chemistry and Life Sciences. Oct. 2-6, 2011, Seattle, Washington, USA.
Griffiths et al., 1994, Isolation of high affinity human antibodies directly from large synthetic repertoires. EMBO J. 13(14):3245-3260.
Moreira et al., 2008, Detection of Salmonella Typhimurium in Raw Meats using In-House Prepared Monoclonal Antibody Coated Magnetic Beads and PCR Assay of the fimA Gene. Journal of Immunoassay & Immunochemistry 29:58-69.
Yeung et al., 2002, Quantitative Screening of Yeast Surface-Displayed Polypeptide Libraries by Magnetic Bead Capture. Biotechnol. 18:212-220.
International Search Report for PCT/US2013/076649 with an International filing date of Dec. 19, 2013, 2 pages.
ISR and Written Opinion in PCT/US2008/058518, dated Sep. 29, 2009, 15 pages.
Gu et al., 2003, Using Biofunctional Magentic Nanoparticles to Capture Vancomycin-Resistant Enterococci and Other Gram-Positive Bacteria at Ultralow Concentration, J. Am. Chem. Soc., 125:15702-15703.
Gu et al., 2006, Biofunctional magnetic nanoparticles for protein separation and pathogen detection, Chem. Commun.:941-949.

(56) References Cited

OTHER PUBLICATIONS

Heijnen et al., 2009, Method for rapid detection of viable *Escherichia coli* in water using real-time NASBA, Water Research, 43:3124-3132.
Li et al., 2010, Chemiluminescent Detect of *E. coli* O157:H7 Using Immunological Method Based on Magnetic Nanoparticles, J. of Nanoscience and Nanotechnology 10:696-701.
Abagram, Principles of Nuclear Magnetism, Carendon Press, Oxford, 1961, pp. 71-83.
Armenean, et al., NMR Radiofrequency Microcoil Design: Electromagnetic Simulation Usefulness, Compes Rendus Biologies, 325(4):457-463 (2002).
Armenean, et al., Solenoidal and Planar Microcoils for NMR Spectroscopy, Proc. of the 25th Annual Int. Conf. of the IEEE Eng. in Med. and Bio. Soc., Cancun, Mexico, Sep. 17, 2003, pp. 3045-3048.
Behnia and Webb, Limited-Sample NMR Using Solenoidal Microcoils, Perfluorocarbon Plugs, and Capillary Spinning, Anal. Chem., 70:5326-5331 (1998).
Byrne, et al., Antibody-Based Sensors: Principles, Problems and Potential for Detection of Pathogens and Associated Toxins, Sensors, 9:4407-4445 (2009).
Chapman, et al., Use of commercial enzyme immunoassays and immunomagnetic separation systems for detecting *Escherichia coli* O157 in bovine fecal samples, Applied and Environmental Microbiology, 63(7):2549-2553 (1997).
Ciobanu and Pennington, 3D Micron-scale MRI of Single Biological Cells, Solid State Nucl. Magn. Reson., 25:138-141 (2004).
Cross, et al., Choice of Bacteria in Animal Models of Sepsis, Infec. Immun. 61(7):2741-2747 (1983).
Djukovic, et al., Signal Enhancement in HPLC/Microcoil NMR Using Automated Column Trapping, Anal. Chem., 78:7154-7160 (2006).
Drancourt, et al., Diagnosis of Mediterranean Spotted Fever by Indirect Immunofluorescence of Rickettsia conorii in circulating Endothelial Cells Isolated with Monoclonal Antibody-Coated Immunomagnetic Beads, J. Infectious Diseases, 166(3):660-663, 1992.
Fan, et al., Self-assembly of ordered, robust, three-dimensional gold nanocrystal/silica arrays, Science, 304:567 (2004).
Fu, et al., Rapid Detection of *Escherichia coli* O157:H7 by Immunogmagnetic Separation and Real-time PCR, Int. J. Food Microbiology, 99(1):47-57, (2005).
Fukushima et al., Experimental Pulse NMR: A Nuts and Bolts Approach, Addison-Wesley, Reading, Mass., 1981.
Goding, J.W., Conjugation of antibodies with fluorochromes: modifications to the standard methods, J. Immunol. Meth., 13:215 (1976).
Goloshevsky, et al., Development of Low Field Nuclear Magnetic Resonance Microcoils, Rev. Sci. Inst.., 76:024101-1 to 024101-6 (2005).
Goloshevsky, et al., Integration of Biaxial Planar Gradient Coils and an RF Microcoil for NMR Flow Imaging, Meas. Sci. Technol., 16:505-512 (2005).
Grant, et al., Analysis of Multilayer Radio Frequency Microcoils for Nuclear Magnetic Resonance Spectroscopy, IEEE Trans. Magn., 37:2989-2998 (2001).
Grant, et al., NMR Spectroscopy of Single Neurons, Magn. Reson. Med., 44:19-22 (2000).
Halbach, Design of Permanent Multipole Magnets with Oriented Rare Earth Cobalt Material, Nuclear Instrum Methods, 169:1-10 (1980).
Harada, et al., Monoclonal antibody G6K12 specific for membrane-associated differentiation marker of human stratified squamous epithelia and squamous cell carcinoma, J. Oral. Pathol. Med., 22(4):1145-152 (1993).
Harlow, et al., 1988, 'Antibodies', Cold Spring Harbor Laboratory, pp. 93-117.

Hijmans, et al., An immunofluorescence procedure for the detection of intracellular immunoglobulins, Clin. Exp. Immunol., 4:457 (1969).
Hirsch, et al., Easily reversible desthiobiotin binding to streptavidin, avidin, and other biotin-binding proteins: uses for protein labeling, detection, and isolation, Anal. Biochem., 208(2):343-57 (2002).
Hoult and Richards, The Signal-to-Noise Ratio of the Nuclear Magnetic Resonance Experiment, J. Magn. Reson., 24:71-85 (1976).
Hunter, et al., Immunoassays for Clinical Chemistry, pp. 147-162, Churchill Livingston, Edinborough (1983).
Inai, et al., Immunohistochemical detection of an enamel protein-related epitope in rat bone at an early stage of osteogenesis, Histochemistry, 99(5):335-362 (1993).
Engvall, Enzyme immunoassay ELISA and EMIT, Meth. in Enzymol., 70:419-439 (1980).
ISR and Written Opinion in PCT/US2008/058518, dated Jul. 7, 2008, 21 pages.
ISR and Written Opinion in PCT/US2008/062473, dated Oct. 29, 2008, 20 pages.
ISR and Written Opinion in PCT/US2008/080983, dated Mar. 3, 2009, 14 pages.
ISR and Written Opinion in PCT/US2009/067577, dated Feb. 5, 2010, 13 pages.
International Search Report in PCT/US2011/33184, dated Jul. 25, 2011, 2 pages.
International Search Report in PCT/US2011/33186, dated Jun. 22, 2011, 1 page.
ISR and Written Opinion in PCT/US2011/48447, dated Dec. 22, 2011, 7 pages.
ISR and Written Opinion in PCT/US2011/48452, dated Dec. 22, 2011, 7 pages.
International Search Report in PCT/US2011/33411, dated Jun. 22, 2011, 1 page.
International Search Report in PCT/US2011/33410, dated Jul. 19, 2011, 2 pages.
Johne, et al., *Staphylococcus aureus* exopolysaccharide in vivo demonstrated by immunomagnetic separation and electron microscopy, J. Clin. Microbiol. 27:1631-1635 (1989).
Johnson, Thermal Agitation of Electricity in Conductors, Phys. Rev., 32:97-109 (1928).
Kaittanis, et al., One-step nanoparticle mediated bacterial detection with magentic relaxation, Nano Lett., 7(2):381-383 (2007).
Lee, et al., Chip-NRM Biosensor for detection and molecular analysis of cells, Nature Medicine, 14(8):869-874 (2008).
Lund, et al. Immunomagnetic separation and DNA hybridization for detection of enterotoxigenic *Escherichia coli* in a piglet model, J. Clin. Microbiol., 29:2259-2262 (1991).
Magin, et aL, Miniature Magnetic Resonance Machines, IEEE Spectrum 34(10):51-61 (1997).
Malba, et al., Laser-lathe Lithography—A Novel Method for Manufacturing Nuclear Magnetic Resonance Microcoils, Biomed. Microdev., 5:21-27 (2003).
Massin, et al., Planar Microcoil-based magnetic resonance imaging of cells, Transducers '03, The 12th Int. Conf. on Solid State Sensors, Actuators, and Microsystems, Boston, Jun. 8-12, pp. 967-970 (2003).
Massin, et al., Planar Microcoil-based Microfluidic NMR Probes, J. Magn. Reson., 164:242-255 (2003).
McDowell, et al., Low-Field Micro-Coil Probe Development for Portable NMR, 8th ICMRM, The Heidelberg Conference, Mibu, Japan, Aug. 22-26, 2005, Conference Program Abstract, 1 page.
McDowell, et al., Operating Nanoliter Scale NMR Microcoils in a Itesla Field, J. Mag. Reson., 188(1):74-82 (2007).
Minard, et al., Solenoidal Microcoil Design, Part I: Optimizing RF Homogeneity and coil dimensions, Concepts in Magn Reson., 13(2):128-142 (2001).
Moresi and Magin, Miniature Permanent Magnet for Table-top NMR, Concept. Magn. Res., 19B:35-43 (2003).
Sista et al., 2008, Heterogeneous Immunoassays Using Magnetic beads on a Digital Microfluidic Platform, Lab Chip 8(2):2188-2196.
Butter et al., 2002, Synthesis and properties of iron ferrofluids, J. Magn. Magn. Mater. 252:1-3.

(56) References Cited

OTHER PUBLICATIONS

Lu et al., 2007, Magnetic Nanoparticles: Synthesis, Protection, Functionalization, and Application, Angew. Chem. Int. Ed. 46:1222-1244.
Matar et al., 1990, Magnetic particles derived from iron nitride, IEEE Transactions on magnetics 26(1):60-62.
Cold Spring Harbor Protocols, Recipe for Dulbecco's phosphate-buffered saline (Dulbecco's PBS, 2009, retrieved from http://cshprotocols.cshlp.Org/content/2009/3/pdb.rec11725. full?text_only=true on Mar. 9, 2015, one page.
Cheng et al, 2012, Concentration and detection of bacteria in virtual environmental samples based on non-immunomagnetic separation and quantum dots by using a laboratory-made system, Proc. of SPIE:82310Y-1-82310Y-18.
Ohno et al, 2011, Effects of Blood Group Antigen-Binding Adhesin Expression during Helicobacter pylori Infection of Mongolian Gerbils, The Journal of Infectious Diseases 203:726-735.
Barany F. (1991) PNAS 88:189-193.
Narang et al., Methods Enzymol., 68:90 (1979).
Brown et al., Methods Enzymol., 68:109 (1979).
DNA Replication 2nd edition, Komberg and Baker, W.H. Freeman, New York, NY (1991).
Barany et al., Gene, 108:1 (1991).
Hinnisdales et al., Biotechniques Res., 19:4193 (1996).
Myers and Gelfand, Biochemistry 30:7661 (1991).
Stenish and McGowan, Biochim Biophys Acta, 475:32 (1977).
Levin, Cell 88:5-8 (1997).
Kleinstruer, "Microfluidics and Nanofluidics: Theory and Selected Applications," John Wiley & Sons, 2013.
Maniatis et al., Molecular Cloning: A Laboratory Manual, 1982, Cold Spring Harbor, NY, pp. 280-281.
Sambrook and Russell, Molecular Cloning: A Laboratory Manual 3Ed, Cold Spring Harbor Laboratory Press, 2001.
Barany, F., Genome research, 1:5-16 (1991).
Margulies et al., Nature, 437: 376-380 (2005).
Olsvik_et_al_Magnetic_Seperation_Techniques_in_Diagnostic_Microbiology_Clinical_Microbiol_Rev_1994_7_43_54.
Chandler et al., Automated immunomagnetic separation and microarray detection of E. Coli O157:H7 from poultry carcass rinse, Int. J. Food Micro., 70 (2001) 143-154.
Bruno et al., "Development of an Immunomagnetic Assay System for Rapid Detection of Bacteria and Leukocytes in Body Fluids," J Mol Recog, 9 (1996) 474-479.
Andreassen, Jack, "One micron magnetic beads optimised for automated immunoassays" as Published in CLI Apr. 2005, retrieved from http://www.cli-online.com/uploads/tx_ttproducts/datasheet/one-micron-magnetic-beads-optimised-for-automatedimmunoassays.pdf on Dec. 28, 2015, four pages.
Safarik et al., "The application of magnetic separations in applied Microbiology" Journal of Applied Bacteriology 1995, 78, 575-585.
Dam et al. "Garlic (*Allium sativum*) Lectins Bind to High Mannose Oligosaccharide Chains", Journal of Biological Chemistry vol. 273, No. 10, Issue of Mar. 6, pp. 5528-5535, 1998.
Fenwick et al., 1986, Mechanisms Involved in Protection Provided by Immunization against Core Lipopolysaccarides of *Escherichia coli* J5 from Lethal Haemophilus pleuropneumoniae Infections in Swine, Infection and Immunity 53(2):298-304.
Yu et al. "Development of a Magnetic Microplate Chemifluorimmunoassay for Rapid Detection of Bacteria and Toxin in Blood", Analytical Biochemistry 261 (1998), pp. 1-7.
The United States Naval Research Laboratory (NRL), "The FABS Device: Magnetic Particles", retrieved from http://www.nrl.navy.mil/chemistry/6170/6177/beads.php on Jan. 8, 2013, two pages.
Life Technologies, "Dynabeads® for Immunoassay IVD", retrieved from http://www.invitrogen.com/site/us/en/home/Productsand-Services/Applications/Diagnostics-Clinical-Research/Bead-based-IVD-Assays/Bead-based-Immunoassay-IVD.html on May 29, 2013, four pages.
Campuzano, et al., Bacterial Isolation by Lectin Modified Microengines, Nano Lett. Jan. 11, 2012; 12(1): 396-401.
Agrawal et al., 1990, Tetrahedron Letters 31:1543-46.
Harkins and Harrigan, "Labeling of Bacterial Pathogens for Flow Cytometric Detection and Enumeration" Curr Prot Cytom (2004) 11.17.1-11.17.20.
Takagi et al., Appl. Environ. Microbiol. 63:4504 (1997).
Cariello et al., Nucl Acids Res, 19:4193 (1991).
Lecomte et al. Nucl Acids Res. 11:7505 (1983).
Cann et al., Proc. Natl. Acad. Sci. 95:14250 (1998).
Braslavsky et al., PNAS, 100:3690-3694 (2003).
Moudrianakis et al., Proc. Natl. Acad. Sci. 53:564-71 (1965).
Vandeventer, J. Clin. Microbiol. Jul. 2011, 49(7):2533-39.
Carroll, N. M., E. E. Jaeger, et al. (2000). "Detection of and discrimination between grampositive and gram-negative bacteria in intraocular samples by using nested PCR." J Clin 15 Microbiol 38(5): 1753-1757.
Klaschik, S., L. E. Lehmann, et al. (2002). "Real-time PCR for detection and differentiation of gram-positive and gram-negative bacteria." J Clin Microbiol 40(11): 4304-4307.
Chien et al., J. Bacteriol, 127:1550 (1976).
Nordstrom et al., J. Biol. Chem. 256:3112 (1981).
Elnifro, Elfath M., et al. "Multiplex PCR: optimization and application in diagnostic virology." Clinical Microbiology Reviews 13.4 (2000): 559-570.
Soni et al., Clin Chem 53:1996-2001 (2007).
Diaz et al., Braz J. Med. Res., 31:1239 (1998).
Verma, Biochim Biophys Acta. 473:1-38 (1977).
Harris et al., Science 320:106-109 (2008).
Dover, Jason E., et al. "Recent advances in peptide probe-based biosensors for detection of infectious agents." Journal of microbiological methods 78.1 (2009): 10-19.

\* cited by examiner

METHODS FOR DEGRADING NUCLEIC ACID

RELATED APPLICATION

The present application claims the benefit of and priority to U.S. provisional patent application Ser. No. 61/739,593 filed Dec. 19, 2012, the content of which is incorporated by reference herein in its entirety.

FIELD OF THE INVENTION

The invention generally relates to methods for degrading nucleic acid.

BACKGROUND

Bioanalytical techniques commonly require reagents, buffers, and equipment that is free of contaminating DNA. Contaminating DNA can interfere with high-sensitivity methods, such as hybrid assay, and can imperil any process that relies upon DNA amplification prior to subsequent analysis, e.g., sequencing. Contaminating DNA can originate from a researcher directly or it can be introduced by way of contaminated surfaces, reagents, buffers, or air. Accordingly, detailed protocols are available for creating "DNA-free workspaces" and for clearing buffers, etc. from contaminating DNA.

A common protocol for providing a "DNA-free workspace" relies on regular bleach washing of all laboratory surfaces and equipment, the use of absorbent bench pads on all surfaces, and the use of dedicated hood space for certain key procedures (e.g., PCR). Other protocols recommend regularly exposing surfaces to UV light in order to degrade or inactivate contaminating DNA. Maintaining a "DNA-free workspace" also involves judicious use of disposable labware, such as pipette tips and sample vials.

In addition to keeping a clean workspace, analytical reagents, washes, and buffers must be free of contaminant DNA. In many cases, this involves procuring "DNA-free" reagents or buffers from manufacturers who prepare the reagents and buffers under strict conditions and perform post-production analysis to assure that no DNA is present. For example DNA-free buffers are available from MoBio (Carlsbad, Calif.). The cost of using certified DNA-free reagents can be substantial, however. For example, 500 ml of DNA-free PBS buffer may cost approximately $50 with shipping.

In other situations, DNA contamination may be removed from reagents, buffers, and samples using DNase and DNase clean-up kits. DNases are endonucleases that catalyze hydrolytic cleavage of phosphodiester linkages in the DNA backbone. A variety of DNases are known, and they may cleave DNA in different places (e.g., ends, mid-chain, specific sequences), or cleave single-stranded DNA over double-stranded DNA, or vice versa. A DNase treatment of a reagent will typically involve introduction of prepared DNase, such as AMBION DNase I (Life Technologies, Carlsbad, Calif.) along with a buffered solution containing substrates and optimized ionic species. In some protocols, it may be necessary to use high-turnover, recombinant DNase, such as TURBO DNase, also available from Life Technologies. After a reagent or sample is treated with DNase, the DNase may be degraded with heat, alcohol, or EDTA in order to prevent interference by the DNase in subsequent processing.

While good laboratory practices and judicious use of DNase can prevent much DNA contamination, some instances of DNA contamination are harder to control. For example, precision instrument components, such as ports, injectors, and columns are not typically disposable because of the high manufacturing costs. Additionally, it may not be possible to easily decontaminate the components using standard techniques (e.g., bleach cleaning) because the cleaning compounds may damage the components. In other situations where direct decontamination is not possible, it may also not be feasible to use DNase to digest contaminant DNA because of concerns over cross-contamination or an inability to deactivate the DNase afterward with heat or alcohol. DNase degradation products may also become a source of contamination in proteomic measurements.

Additionally, reliance on certified DNA-free reagents and disposable labware is expensive and produces a large amount of solid waste.

SUMMARY

The invention generally provides methods for degrading nucleic acid. Methods of the invention are useful for decontaminating labware, reagents, buffers, and samples. Aspects of the invention are accomplished using reactive oxygen species to degrade nucleic acid. An advantage of the reactive oxygen species is their efficiency of degrading nucleic acid and the ease by which the decontaminating solution can be cleared so that sample nucleic acid is not affected by the decontaminating solution.

The reactive oxygen species can be easily produced using reactions between metal ions ($Fe^{2+}$, $Fe^{3+}$) and hydrogen peroxide ($H_2O_2$). The reactive oxygen species may include peroxides ($O_2^{2-}$), superoxides ($O_2^-$), and hydroxyl radicals (OH.), however the exact mixture of the reactive oxygen species may change with time and pH. Using metal ion and peroxide solutions, a buffer or reagent can be quickly and efficiently cleared of nucleic acid. After nucleic acid clearance, the buffer may be heated to dissociate remaining $H_2O_2$ or exposed to an ion exchange resin or chelating agent to remove or sequester the metal ions. The method is also useful for decontaminating laboratory equipment, separation media, and supports for separation media, such as magnetic beads.

In one instance, the invention is a method for degrading contaminant DNA associated with a separation medium or support. The method includes contacting the separation medium or support with a solution comprising metal ions and peroxide ions. The metal ions are selected from iron, manganese, copper, nickel, and cobalt, however they are typically iron, such as $Fe^{2+}$ ions or $Fe^{3+}$ ions. Typically, the separation medium or support is allowed to contact the solution comprising metal ions and peroxide ions for some time and then the decontamination solution is deactivated. The solution can be deactivated by raising the temperature of the solution to dissociate hydrogen peroxide or the solution can be deactivated by binding the metal ions with an ion-exchange medium or a chelating agent. In a specific embodiment, the separation medium or support is decontaminated with a solution comprising hydrogen peroxide and $Fe_2(SO_4)_3$.

In another instance, the invention is a method for clearing contaminant DNA from a buffer solution, analytical reagent, or sample. The method includes adding metal ions and peroxide ions to the buffer solution, analytical reagent, or sample and later heating the buffer solution, analytical reagent, or sample to dissociate the peroxide ions. In another embodiment, the method includes adding metal ions and peroxide ions to the buffer solution, analytical reagent, or sample and later binding the metal ions.

Using the methods described herein, it is possible to inexpensively and effectively remove contaminant DNA from labware, reagents, buffers, samples, laboratory equipment, separation media, and supports. Use of the methods of the invention will reduce measurement, amplification, and sequencing errors resulting from contaminant DNA.

DETAILED DESCRIPTION

The invention provides alternative methods for removing contaminant DNA from reagents, labware, and laboratory equipment. Unwanted DNA is a common source of error in bioanalytical analysis, and constant vigilance is needed when using techniques, such as PCR, where minute amounts of DNA can compromise measurements. As discussed above, while DNase may be used to decontaminate some buffers and samples, there are instances where DNase clean-up is not feasible. Additionally, bleach decontamination may not be feasible because of inaccessibility to key instrument components or reactivity with the cleaning products.

The invention uses reactive oxygen species, and reactions that produce reactive oxygen species, to oxidize and degrade DNA present in reagents, buffers, samples, and on laboratory equipment. The methods disclosed involve combining reactive oxygen species, such as hydrogen peroxide, with metal ions, such as $Fe^{2+}$. The reagents are inexpensive, easy to combine, and the remnants of the reaction are easily removed from the reagents, buffers, etc. after degradation of DNA.

Oxidative species are recognized as a source of genetic mutation. The reactive oxygen species implicated in metal-ion degradation of DNA include peroxides ($O_2^{2-}$), superoxides ($O_2^-$), singlet oxygen ($O_2^*$), and hydroxyl radicals (OH.). The complete mechanism for the formation of the reactive oxygen species in the presence of metal ions has not been elucidated. However, it is time and pH-dependent, and likely includes some or all of the following reactions (M=metal ion, e.g., Fe):

$$O_2 + e^- \rightarrow O_2^- \quad (1)$$

$$2H_2O_2 \rightarrow 2H_2O + O_2 \quad (2)$$

$$2O_2^- + 2H^+ \rightarrow O_2 + H_2O_2 \quad (3)$$

$$O_2^- + M^{3+} \rightarrow M^{2+} + O_2 \quad (4)$$

$$M^{2+} + H + H_2O_2 \rightarrow M^{3+} + OH. + H_2O \quad (5)$$

$$M^{2+} + H_2O_2 \rightarrow M^{3+} + OH. + OH^- \quad (6)$$

$$M^{2+} + H_2O_2 \rightarrow MO_2^+ + H_2O \quad (7)$$

$$MO_2^+ + H^+ \rightarrow MOH^{3+} \rightarrow M^{3+} + OH. \quad (8)$$

$$M^{3+} + H_2O_2 \rightarrow MOOH^{2+} + H^+ \rightarrow M^{2+} + 2H^+ + O_2^- \quad (9)$$

$$M^{3+} + H_2O_2 \rightarrow M^{2+} + H^+ + OOH^- \quad (10)$$

See Henle and Linn, "Formation, Prevention, and Repair of DNA Damage by Iron/Hydrogen Peroxide," *J. Bio. Chem.*, vol. 272, 19095-19098 (1997), incorporated by reference herein in its entirety.

A number of different metal ions may react with activated oxygen species through combinations of reactions 1-10 above. The metals ions include iron, manganese, copper, nickel, cobalt, or zinc. The oxidation state of the ions may be +1, +2, +3, +4, or +5, however, +2 and +3 ions are most involved in the creation of reactive oxygen species. Other oxidation states, e.g., +1, +4, +5, are achieved through oxidation or reduction with other species. Because a variety of metal ions may participate in the degradation pathway, DNA protocols often call for the sequestering of metal ions, e.g., with EDTA, to avoid these degradation processes.

Research suggests that DNA degradation in the presence of reactive oxygen species is primarily driven by abstraction of hydrogen atoms from the sugar phosphate backbone. In particular, the hydrogen atom attached to the C5' carbon of the deoxyribose sugar is most available in double-stranded DNA, and most likely to react with a reactive oxygen species. Accordingly, cleavage of the bond between the C5' and C6' atoms is most often observed.

Nonetheless, upon removal of a hydrogen atom, a deoxyribose carbocation may undergo one or more rearrangements prior to cleavage. Upon rearrangement, the molecule may cleave at another point in the deoxyribose molecule, i.e., not between the C5' and C6' atoms. Furthermore, the stability of the carbocation (or rearrangement product) influences the equilibrium between reactants (DNA+oxidative species) and products (broken chain+water). In particular, the lack of stable carbocation products for ribose sugars explains why RNA is much less susceptible to oxidative degradation than DNA. See Gates, "The Chemical Reactions of DNA Damage and Degradation," *Reviews of Reactive Intermediate Chemistry*, Platz et al., eds., p. 351-356 (2007), incorporated herein by reference.

In addition to abstracting hydrogen from the deoxyribose sugar, oxidative species may also damage DNA bases. In particular, the N7 to C8 bond in the purine moiety (adenine and guanine) and the C5 to C6 bond in the pyrimidine moiety (cytosine and thymine) are susceptible cleavage by oxidative species. Because these cleavages do not break the sugar phosphate chain, the cleavages may not lead to degradation of the DNA chain, and the bases may be repaired in subsequent processing steps. Among bases, cytosine is most likely damaged by oxidative species, followed by thymine, followed by adenine, followed by guanine. See Henle et al., "Oxidative Damage to DNA Constituents by Iron-mediated Fenton Reactions," *J. Bio. Chem.*, vol. 271, p. 21177-86 (1996), incorporated herein by reference. Other mechanisms, including radical-metal attachment chemistry, have also been implicated in DNA degradation. See Henle and Lin.

Methods of the invention include addition of metal ions and oxidative species to reagents, buffers, and samples. In most instances, metal ions of the desired oxidation state are readily available as salts, for example $FeCl_3$, $Fe_2(SO_4)_3$, $Fe(SO_4)$, and $(NH_4)_2Fe(SO_4)_6$. High purity metal salts are available from chemical suppliers such as Sigma-Aldrich (St. Louis, Mo.). In some instances, the metal salts are water soluble. In other instances, the aqueous solubility of the metal salts is increased with the addition of acid, for example hydrochloric acid or sulfuric acids, or with the addition of alcohols. Metal salts that may be used with methods of the invention include copper salts such as $Cu_2S$, CuS, $Cu(CH_3COO)_2$, and $Cu(SO_4)$; manganese salts such as $Mn(CO_3)$ and $Mn(SO_4)$; nickel salts such as $NiCl_6$, $(NiCl_4)SO_4$, and $Ni(SO_4)$; and cobalt salts such as $Co(SO_4)$. In some embodiments, a final concentration of metal ions is 1 μM or greater, e.g., 10 μM or greater, e.g., 100 μM or greater, e.g., 1 mM or greater, e.g., 10 mM or greater, e.g., 100 mM or greater. Because the metal ions are not consumed during the degradation, the concentration of the metal ions before and after degradation should be approximately equivalent.

The oxidative species are typically initiated by adding $H_2O_2$ to the reagents, buffers, or samples containing the DNA contaminants. Aqueous $H_2O_2$ solutions are available from chemical suppliers such as Sigma-Aldrich at a variety of concentrations, e.g., 3%, 10%, 30%. When metal ions are also present in a solution to which hydrogen peroxide is added, a number of oxidative species are created, as outlined above. The oxidative species, in turn degrade the DNA, as described above. In some embodiments, the initial concentration of $H_2O_2$ in the reagent, buffer, or sample is 1 µM or greater, e.g., 10 µM or greater, e.g., 100 µM or greater, e.g., 1 mM or greater, e.g., 10 mM or greater, e.g., 100 mM or greater. Because the $H_2O_2$ is consumed during the degradation process, the final concentration of $H_2O_2$ is typically smaller than the initial concentration of $H_2O_2$. The initial molar ratio of metal ions to peroxide ions in the solution may be between about 1:1 and about 1:50, e.g., about 1:1 to about 1:25, e.g., about 1:1 to about 1:10, e.g., about 1:5 to about 1:10.

In embodiments where it is feasible to adjust the pH (i.e., not buffers), the conditions of the DNA degradation may be adjusted by modifying the pH of the solution. This may be accomplished with the direct addition of acids (e.g., hydrochloric acid, sulfuric acid, or acetic acid) or bases (e.g., sodium hydroxide, potassium hydroxide). It may also be accomplished with the addition of acid- or base-generating species (e.g., chlorine gas, or sodium hypochlorite). In some embodiments, the pH of a degradation solution or a regent being decontaminated will be greater than or equal to pH=3, e.g., greater than or equal to pH=4, e.g., greater than or equal to pH=5, e.g., greater than or equal to pH=6, e.g., greater than or equal to pH=7, e.g., greater than or equal to pH=8, e.g., greater than or equal to pH=9, e.g., greater than or equal to pH=10, e.g., greater than or equal to pH=11, e.g., pH=12. In some embodiments, the pH of a degradation solution or a regent being decontaminated will be less than or equal to pH=12, e.g., less than or equal to pH=11, e.g., less than or equal to pH=10, e.g., less than or equal to pH=9, e.g., less than or equal to pH=8, e.g., less than or equal to pH=7, e.g., less than or equal to pH=6, e.g., less than or equal to pH=5, e.g., less than or equal to pH=4, e.g., pH=3. The solution may have a pH of from about 3 to about 12, e.g., from about 4 to about 11, e.g., from about 5 to about 10, e.g., from about 6 to about 9, e.g., from about 6 to about 8, e.g., about 7.

Prior to using the newly-prepared DNA-free reagents, buffers, or samples, it will often be necessary to remove excess oxidative species and/or metal ions. Typically, any excess $H_2O_2$ can be removed by heating the solution, thereby increasing the rate at which $H_2O_2$ dissociates into oxygen gas and water (see equation 2 above). With the removal of excess $H_2O_2$, there are few sources for additional oxidative species, and the degradation reactions will quickly terminate once the other oxidative species (e.g., superoxides, hydroxyl radicals) have reacted. In one embodiment, a reagent, buffer, or sample will be heated to at least about 35° C., e.g., at least about 40° C., e.g., at least about 45° C., e.g., at least about 50° C., e.g., at least about 55° C., e.g., at least about 60° C., e.g., at least about 65° C., e.g., at least about 70° C., e.g., at least about 75° C., e.g., at least about 80° C., e.g., at least about 85° C. The reagent, buffer, or sample will be heated for at least about 5 minutes, e.g., at least about 10 minutes, e.g., at least about 15 minutes, e.g., at least about 20 minutes, e.g., at least about 30 minutes, e.g., at least about 60 minutes. When samples containing proteins or RNA are being decontaminated, it is important to monitor the temperature of the solution during the decontamination so that the proteins or RNA are not damaged. For example, the solution may be kept at a temperature between 35 and 45° C. for a period of time to assure that all $H_2O_2$ is dissociated, but that the proteins or RNA remain, for the most part, intact.

In some heat-sensitive applications, it may be necessary to use enzymes that facilitate dissociation of oxidative species, such as superoxides, to deactivate reactive oxygen species. Enzymes such as superoxide dismutases (SODs) may be used to "turn off" the reactions once the degradation is complete. SOD is commercially available from Sigma-Aldrich. SOD may also sequester free metal ions, which are cofactors to the dissociate reactions, however this is not the dominant mechanism for reducing oxidative degradation. While SOD administration is an option for terminating oxidative degradation reactions, it is expensive and results in many of the same complications seen with the use of DNase (discussed above).

In addition to removing the oxidative species, e.g., $H_2O_2$, it may be beneficial to remove metal ions from the reagents, buffers, or samples after the degradation process is complete. Free metal ions can be removed using a number of known techniques, and some techniques will be better than others depending upon the intended use of the reagents, buffers, or samples. In one embodiment, the metal ions may be removed using an ion-exchange column, such as available from GE Healthcare Biosciences (Pittsburgh, Pa.). Using ion-exchange chromatography the reagents, buffers, or samples are put in contact with a stationary phase having ionic functional groups that bind ions of opposite charge, e.g., $M^{2+}$. The reagents, buffers, or samples either pass through the stationary phase, as in a column, or the reagents, buffers, or samples are agitated with the stationary phase and then the stationary phase removed, decanted, etc.

In another embodiment, the free metal ions can be removed using chelating agents such as EDTA, citric acid, or phosphonates. Chelating agents are widely available from chemical suppliers such as Sigma-Aldrich. In some instances, the chelating agents do not remove the metal ions from the reagents, buffers, or samples, but rather deactivate them by forming complexes which remain in the solution. In other instances, the chelating agents cause the metal ions to precipitate from solution. The precipitate may be removed with filtering, for example.

The methods of the invention may also be used to decontaminate laboratory equipment, including labware, scientific instruments, and portions thereof. For example, an aqueous degradation solution comprising $Fe_2(SO_4)_3$ and $H_2O_2$ may be prepared and the laboratory equipment allowed to soak (incubate) in the solution for some time, e.g., 1 hour or longer, 2 hours or longer, 4 hours or longer, 8 hours or longer, 12 hours or longer, or 24 hours or longer. After soaking, the laboratory equipment can be rinsed (soaked, incubated) with DNA-free water, and then allowed to dry in a DNA-free hood or baked in an oven.

In some instances, an aqueous solution comprising $Fe_2(SO_4)_3$ and $H_2O_2$ can be used to decontaminate separation media, such as polymer beads or magnetic beads. In other embodiments, an aqueous solution comprising $Fe_2(SO_4)_3$ and $H_2O_2$ can be used to decontaminate a support, i.e., the precursor to the separation medium. After preparation of a degradation solution, the separation media can be allowed to soak in the solution for some time, e.g., 1 hour or longer, 2 hours or longer, 4 hours or longer, 8 hours or longer, 12 hours or longer, or 24 hours or longer. In instances where the separation media is packed, e.g., in a column, it may be sufficient to add the degradation solution directly to the column and allow the separation media to soak in the presence of the degradation solution for some time, e.g., 1 hour or longer, 2 hours or longer, 4 hours or longer, 8 hours or longer, 12 hours or longer, or 24 hours or longer. The separation media can be rinsed with DNA-free water, and then allowed to dry in a DNA-free hood or baked in an oven. In some instances the separation media will be decontaminated prior to activation or binding of ligands e.g., antibodies. In other instances, the separation media will be decontaminated after the separation media has been activated or ligands bound thereto.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for degrading nucleic acid, the method comprising:
   contacting nucleic acid with a solution comprising adding metal ions and peroxide ions to degrade the nucleic acid, such that the nucleic acid is not available for amplification; and
   binding the metal ions subsequent to degradation of the nucleic acid.

2. The method of claim 1, wherein the metal ion to peroxide ion molar ratio is from about 1:1 to about 1:25.

3. The method of claim 1, wherein the metal ion to peroxide ion molar ratio is from about 1:5 to about 1:10.

4. The method of claim 1, wherein the nucleic acid is associated with a separation medium or a solid support.

5. The method of claim 4, wherein the solid support is a bead.

6. The method of claim 5, wherein the bead is a type selected from the group consisting of magnetic, paramagnetic, ferromagnetic, and a combination thereof.

7. The method of claim 4, wherein the solid support is a planar substrate.

8. The method of claim 4, further comprising removing the separation media or support from the solution and subsequently rinsing the separation media or support with an aqueous solution.

9. The method of claim 1, wherein the metal ions are selected from the group consisting of iron, manganese, copper, nickel, and cobalt.

10. The method of claim 9, wherein the metal ions are $Fe^{2+}$ ions or $Fe^{3+}$ ions or a combination thereof.

11. The method of claim 1, wherein the solution comprises hydrogen peroxide.

12. The method of claim 1, wherein the solution has a pH of about 3 to about 12.

13. The method of claim 12, wherein the solution has a pH of about 3 to about 6.

14. The method of claim 1, wherein the solution has a concentration of about 1 mM or greater of metal ions.

15. The method of claim 1, wherein contacting lasts for at least about 10 minutes.

16. The method of claim 15, wherein contacting lasts for at least about 60 minutes.

17. The method of claim 1, further comprising heating the solution to dissociate peroxide ions.

18. The method of claim 17, wherein the temperature of the solution is raised to at least about 40° C.

19. The method of claim 1, wherein binding comprises contacting the solution with an ion-exchange medium or chelating agent.

20. The method of claim 1, wherein the solution is an aqueous solution comprising hydrogen peroxide and $Fe_2(SO_4)_3$.

21. The method of claim 1, wherein binding comprises contacting the solution with an ion-exchange medium or chelating agent.

22. A method for degrading nucleic acid, such that the nucleic acid is unavailable for amplification, the method comprising:
   contacting nucleic acid with a solution comprising metal ions and peroxide ions; and
   heating the solution to dissociate the peroxide ions for at least about 15 minutes; and
   binding the metal ions subsequent to degradation of the nucleic acid.

23. The method of claim 22, wherein a temperature of the solution is raised to at least about 40° C.

24. The method of claim 22, wherein binding comprises contacting the solution with an ion-exchange medium or chelating agent.

25. The method of claim 22, wherein the metal ions are $Fe^{2+}$ ions or $Fe^{3+}$ ions or a combination thereof.

26. The method of claim 22, further comprising adjusting a pH of the solution to between about 3 and 12.

* * * * *